(12) United States Patent
Pinsonneault

(10) Patent No.: US 8,392,214 B1
(45) Date of Patent: Mar. 5, 2013

(54) SYSTEMS AND METHODS FOR FACILITATING CLAIM REJECTION RESOLUTION BY PROVIDING PRIOR AUTHORIZATION ASSISTANCE

(75) Inventor: Roger Pinsonneault, Alpharetta, GA (US)

(73) Assignee: McKesson Financial Holdings Limited (BM)

( * ) Notice: Subject to any disclaimer, the term of this patent is extended or adjusted under 35 U.S.C. 154(b) by 204 days.

(21) Appl. No.: 12/957,106

(22) Filed: Nov. 30, 2010

(51) Int. Cl.
*G06Q 50/00* (2012.01)

(52) U.S. Cl. ......... 705/2; 705/3; 705/4; 705/32; 705/50; 235/378

(58) Field of Classification Search ................ 705/2, 3, 705/4, 32, 50; 235/378
See application file for complete search history.

(56) References Cited

U.S. PATENT DOCUMENTS

| | | | |
|---|---|---|---|
| 4,674,041 A | 6/1987 | Lemon et al. | |
| 4,723,212 A | 2/1988 | Mindrum et al. | |
| 4,910,672 A | 3/1990 | Off et al. | |
| 5,007,641 A | 4/1991 | Seidman | |
| 5,080,364 A | 1/1992 | Seidman | |
| 5,173,851 A | 12/1992 | Off et al. | |
| 5,201,010 A | 4/1993 | Deaton et al. | |
| 5,237,620 A | 8/1993 | Deaton et al. | |
| 5,305,196 A | 4/1994 | Deaton et al. | |
| 5,327,508 A | 7/1994 | Deaton et al. | |
| 5,388,165 A | 2/1995 | Deaton et al. | |
| 5,430,644 A | 7/1995 | Deaton et al. | |
| 5,448,471 A | 9/1995 | Deaton et al. | |
| 5,588,649 A | 12/1996 | Blumberg et al. | |
| 5,592,560 A | 1/1997 | Deaton et al. | |
| 5,612,868 A | 3/1997 | Off et al. | |
| 5,621,812 A | 4/1997 | Deaton et al. | |
| 5,628,530 A | 5/1997 | Thornton | |
| 5,638,457 A | 6/1997 | Deaton et al. | |
| 5,642,485 A | 6/1997 | Deaton et al. | |

(Continued)

FOREIGN PATENT DOCUMENTS

| CA | 2482370 A1 | 3/2006 |
|---|---|---|
| WO | WO 9503569 A3 | 2/1995 |

(Continued)

OTHER PUBLICATIONS

Google patents search, Sep. 11, 2012.*

(Continued)

*Primary Examiner* — Dilek B Cobanoglu
(74) *Attorney, Agent, or Firm* — Sutherland Asbill & Brennan LLP

(57) ABSTRACT

Systems and methods are provided for providing prior authorization support. The systems and methods may include receiving a first request for prior authorization assistance from a pharmacy computer, wherein the request for assistance includes claim identification information for a prior healthcare claim transaction; identifying a stored transaction history record for the prior healthcare claim transaction, where the stored transaction record is identified based at least in part on the claim identification information, where the stored transaction history record indicates a denial of coverage by a payor of a drug or product for a patient; delivering, to a prior authorization assistance computer, a second request for prior authorization assistance, where the information included in the second request enables the prior authorization assistance computer to initiate a process for completing a prior authorization form and for delivering the completed form to the payor; and delivering, to the pharmacy computer, a response indicating acceptance of the first request for assistance.

20 Claims, 8 Drawing Sheets

U.S. PATENT DOCUMENTS

| | | | |
|---|---|---|---|
| 5,644,723 | A | 7/1997 | Deaton et al. |
| 5,649,114 | A | 7/1997 | Deaton et al. |
| 5,659,469 | A | 8/1997 | Deaton et al. |
| 5,675,662 | A | 10/1997 | Deaton et al. |
| 5,687,322 | A | 11/1997 | Deaton et al. |
| 5,832,457 | A | 11/1998 | O'Brien |
| 5,845,255 | A | 12/1998 | Mayaud |
| 5,857,175 | A | 1/1999 | Day et al. |
| 5,892,827 | A | 4/1999 | Beach et al. |
| 5,915,007 | A | 6/1999 | Klapka |
| 5,926,795 | A | 7/1999 | Williams |
| 5,970,469 | A | 10/1999 | Scroggie et al. |
| 5,974,399 | A | 10/1999 | Giuliani et al. |
| 6,012,035 | A | 1/2000 | Freeman, Jr. et al. |
| 6,014,634 | A | 1/2000 | Scroggie et al. |
| 6,021,392 | A | 2/2000 | Lester et al. |
| 6,026,370 | A | 2/2000 | Jermyn |
| 6,041,309 | A | 3/2000 | Laor |
| 6,055,573 | A | 4/2000 | Gardenswartz et al. |
| 6,067,069 | A | 5/2000 | Krause |
| 6,067,524 | A | 5/2000 | Byerly et al. |
| 6,088,677 | A | 7/2000 | Spurgeon |
| 6,185,541 | B1 | 2/2001 | Scroggie et al. |
| 6,195,612 | B1 | 2/2001 | Pack-Harris |
| 6,202,923 | B1 | 3/2001 | Boyer et al. |
| 6,205,455 | B1 | 3/2001 | Umen |
| 6,240,394 | B1 | 5/2001 | Uecker |
| 6,260,758 | B1 | 7/2001 | Blumberg |
| 6,278,979 | B1 | 8/2001 | Williams |
| 6,282,516 | B1 | 8/2001 | Giuliani |
| 6,298,330 | B1 | 10/2001 | Gardenswartz et al. |
| 6,304,849 | B1 | 10/2001 | Uecker et al. |
| 6,307,958 | B1 | 10/2001 | Deaton et al. |
| 6,321,210 | B1 | 11/2001 | O'Brien et al. |
| 6,334,108 | B1 | 12/2001 | Deaton et al. |
| 6,377,935 | B1 | 4/2002 | Deaton et al. |
| 6,424,949 | B1 | 7/2002 | Deaton et al. |
| 6,484,146 | B2 | 11/2002 | Day et al. |
| 6,584,448 | B1 | 6/2003 | Laor |
| 6,684,195 | B1 | 1/2004 | Deaton et al. |
| 6,757,898 | B1 | 6/2004 | Ilsen et al. |
| 6,769,228 | B1 | 8/2004 | Mahar |
| 6,795,809 | B2 | 9/2004 | O'Brien et al. |
| 6,885,994 | B1 | 4/2005 | Scroggie et al. |
| 7,024,374 | B1 | 4/2006 | Day et al. |
| 7,058,584 | B2 | 6/2006 | Kosinski et al. |
| 7,058,591 | B2 | 6/2006 | Giuliani et al. |
| 7,155,397 | B2 | 12/2006 | Alexander et al. |
| 7,225,052 | B2 | 5/2007 | Foote et al. |
| 7,228,285 | B2 | 6/2007 | Hull et al. |
| 7,233,913 | B2 | 6/2007 | Scroggie et al. |
| 7,309,001 | B2 | 12/2007 | Banfield et al. |
| 7,415,426 | B2 | 8/2008 | Williams et al. |
| 7,426,480 | B2 | 9/2008 | Granger et al. |
| 7,685,006 | B2 | 3/2010 | Rahn et al. |
| 7,926,709 | B1 | 4/2011 | Dooley et al. |
| 2002/0002495 | A1 | 1/2002 | Ullman |
| 2002/0087583 | A1 | 7/2002 | Morgan et al. |
| 2002/0111832 | A1 | 8/2002 | Judge |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0074218 | A1 | 4/2003 | Liff et al. |
| 2003/0125986 | A1 | 7/2003 | Collosi |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0039599 | A1 | 2/2004 | Fralic |
| 2004/0049422 | A1 | 3/2004 | Mortimer |
| 2004/0054657 | A1 | 3/2004 | Takeyama |
| 2004/0054685 | A1 | 3/2004 | Rahn et al. |
| 2004/0073457 | A1 | 4/2004 | Kalies |
| 2004/0078234 | A1 | 4/2004 | Tallal, Jr. et al. |
| 2004/0107117 | A1 | 6/2004 | Denny |
| 2004/0111277 | A1 | 6/2004 | Pearson et al. |
| 2004/0117323 | A1 | 6/2004 | Mindala |
| 2004/0148198 | A1 | 7/2004 | Kalies |
| 2004/0153336 | A1 | 8/2004 | Virdee et al. |
| 2004/0249745 | A1 | 12/2004 | Baaren |
| 2005/0015280 | A1 | 1/2005 | Gabel et al. |
| 2005/0033610 | A1 | 2/2005 | Cunningham |
| 2005/0060201 | A1 | 3/2005 | Connely, III et al. |
| 2005/0086081 | A1 | 4/2005 | Brock-Fisher |
| 2005/0090425 | A1 | 4/2005 | Reardan et al. |
| 2005/0102169 | A1 | 5/2005 | Wilson |
| 2005/0154627 | A1 | 7/2005 | Zuzek et al. |
| 2005/0171815 | A1 | 8/2005 | Vanderveen |
| 2005/0187793 | A1 | 8/2005 | Myles |
| 2005/0197862 | A1 | 9/2005 | Paterson et al. |
| 2005/0240473 | A1 | 10/2005 | Ayers, Jr. et al. |
| 2005/0288972 | A1 | 12/2005 | Marvin et al. |
| 2006/0015518 | A1 | 1/2006 | Eletreby et al. |
| 2006/0020514 | A1 | 1/2006 | Yered |
| 2006/0026041 | A1 | 2/2006 | Ullman |
| 2006/0149587 | A1 | 7/2006 | Hill, Sr. et al. |
| 2006/0149784 | A1 | 7/2006 | Tholl et al. |
| 2006/0184391 | A1 | 8/2006 | Barre et al. |
| 2006/0224415 | A1 | 10/2006 | Hudson et al. |
| 2006/0229915 | A1 | 10/2006 | Kosinski et al. |
| 2006/0259363 | A1 | 11/2006 | Jhetam et al. |
| 2006/0271398 | A1 | 11/2006 | Belcastro |
| 2006/0287886 | A1 | 12/2006 | Kitazawa |
| 2007/0005402 | A1 | 1/2007 | Kennedy et al. |
| 2007/0050209 | A1 | 3/2007 | Yered |
| 2007/0088576 | A1 | 4/2007 | de Beus et al. |
| 2007/0124177 | A1 | 5/2007 | Engleson et al. |
| 2007/0136100 | A1 | 6/2007 | Daugherty et al. |
| 2007/0179957 | A1 | 8/2007 | Gibson et al. |
| 2007/0233525 | A1 | 10/2007 | Boyle |
| 2007/0233526 | A1 | 10/2007 | Hoffman et al. |
| 2007/0239493 | A1 | 10/2007 | Sweetland et al. |
| 2009/0198518 | A1* | 8/2009 | McKenzie et al. ................ 705/3 |
| 2011/0178812 | A1 | 7/2011 | Lindsay |

FOREIGN PATENT DOCUMENTS

| | | | |
|---|---|---|---|
| WO | WO 0039737 | A1 | 7/2000 |
| WO | WO 2007025295 | A2 | 3/2007 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Non-Final Office Action for U.S. Appl. No. 12/605,946 mailed Mar. 21, 2012.

Non-Final Office Action for U.S. Appl. No. 12/605,946 mailed Dec. 9, 2011.

Non-Final Office Action for U.S. Appl. No. 13/071,567, mailed Oct. 5, 2012.

* cited by examiner

SYSTEMS AND METHODS FOR FACILITATING CLAIM REJECTION RESOLUTION BY PROVIDING PRIOR AUTHORIZATION ASSISTANCE

FIELD OF THE INVENTION

Aspects of the invention relate generally to facilitating claim rejection resolution, and more specifically, to systems and methods for facilitating claim rejection resolution by providing prior authorization assistance.

BACKGROUND OF THE INVENTION

Claim rejections and requirements for prior authorizations can be used by third-party payors as a cost-containment measure. While claim rejections and requirements for prior authorizations can provide for cost-containment measures, they can result in denials of coverage, which require significant efforts by patients, pharmacists, physicians, or other healthcare providers to resolve. In addition, patients may choose to abandon medical treatment based upon denials of coverage by payors. Accordingly, there is an opportunity for systems and methods for facilitating claim rejection resolution by providing prior authorization assistance.

SUMMARY OF THE INVENTION

According to an example embodiment of the invention, there is a method. The method may include receiving a first request for prior authorization assistance from a pharmacy computer associated with a pharmacy, wherein the request for prior authorization assistance includes claim identification information for a prior healthcare claim transaction; identifying a stored transaction history record for the prior healthcare claim transaction, wherein the stored transaction record is identified based at least in part on the claim identification information from the request for prior authorization assistance, wherein the stored transaction history record indicates a denial of coverage by a payor of a drug or product for a patient; preparing a second request for prior authorization assistance, the second request based at least in part on information from the stored transaction history record, wherein the second request identifies at least patient information, identification of the drug or product for the patient, and identification of the payor; delivering, to a prior authorization assistance computer, the second request for prior authorization assistance, wherein the information included in the second request enables the prior authorization assistance computer to initiate a process for completing a prior authorization form and for delivering the completed prior authorization form to the payor; and delivering, to the pharmacy computer, a response indicating acceptance of the first request for prior authorization assistance, wherein the response is stylized as a paid response or a rejection response based upon preferences of the pharmacy. One or more of the prior steps may be performed by one or more computers associated with a service provider.

According to another example embodiment of the invention, there is a system. The system may include at least one memory for storing computer-executable instructions; and at least one processor configured to access the at least one memory. The at least one processor may be configured to execute the computer-executable instructions to: receive a first request for prior authorization assistance from a pharmacy computer associated with a pharmacy, wherein the request for prior authorization assistance includes claim identification information for a prior healthcare claim transaction; identify a stored transaction history record for the prior healthcare claim transaction, wherein the stored transaction record is identified based at least in part on the claim identification information from the request for prior authorization assistance, wherein the stored transaction history record indicates a denial of coverage by a payor of a drug or product for a patient; prepare a second request for prior authorization assistance, the second request based at least in part on information from the stored transaction history record, wherein the second request identifies at least patient information, identification of the drug or product for the patient, and identification of the payor; deliver, to a prior authorization assistance computer, the second request for prior authorization assistance, wherein the information included in the second request enables the prior authorization assistance computer to initiate a process for completing a prior authorization form and for delivering the completed prior authorization form to the payor; and deliver, to the pharmacy computer, a response indicating acceptance of the first request for prior authorization assistance, wherein the response is stylized as a paid response or a rejection response based upon preferences of the pharmacy.

BRIEF DESCRIPTION OF THE DRAWINGS

Reference will now be made to the accompanying drawings, which are not necessarily drawn to scale, and wherein.

DETAILED DESCRIPTION

Embodiments of the invention will be described more fully hereinafter with reference to the accompanying drawings, in which embodiments of the invention are shown. This invention may, however, be embodied in many different forms and should not be construed as limited to the embodiments set forth herein; rather, these embodiments are provided so that the disclosure will be thorough and complete, and will fully convey the scope of the invention to those skilled in the art. Like numbers refer to like elements throughout.

System Overview

Figure 1:
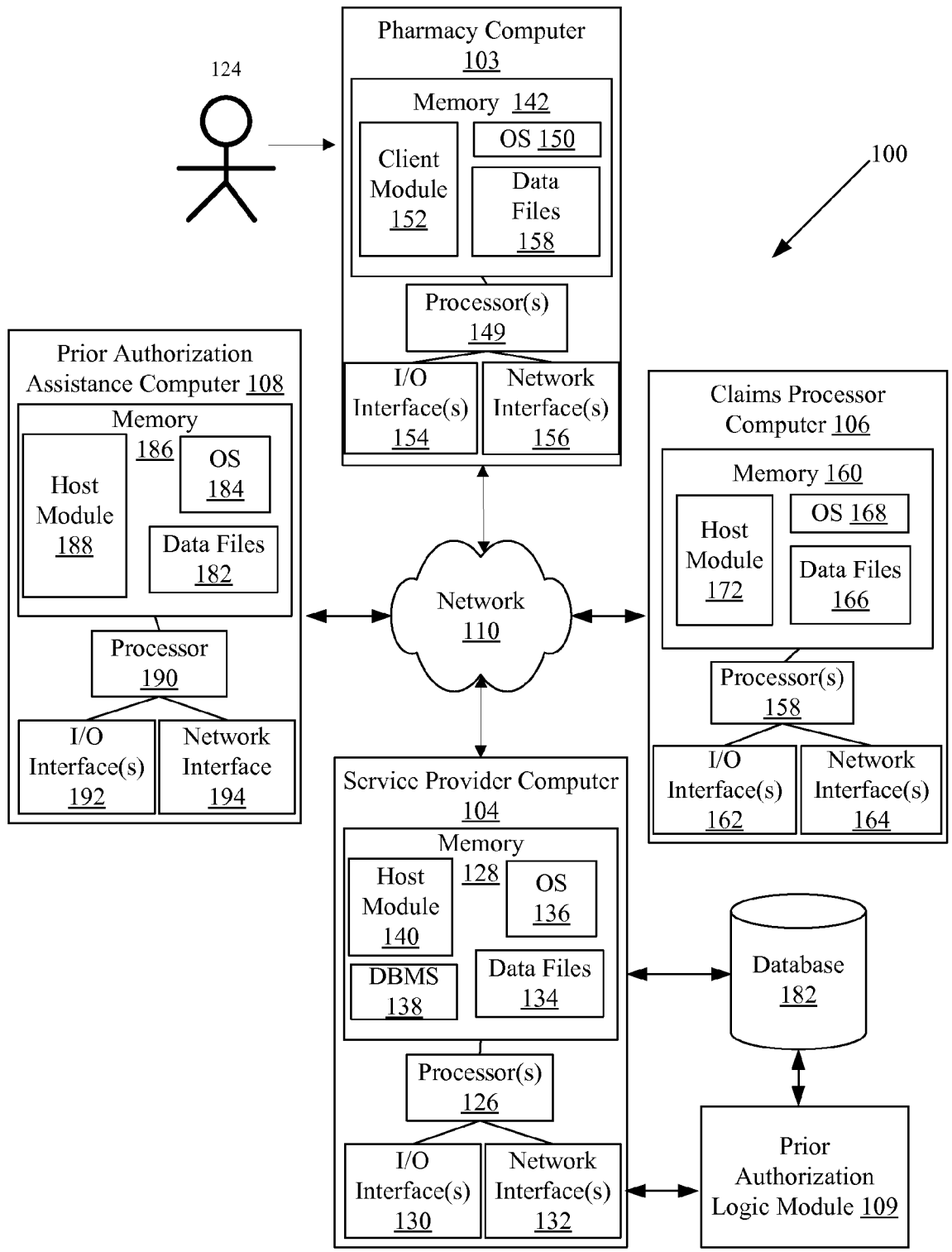
FIG. 1 illustrates an example healthcare system for facilitating claim rejection resolution by providing prior authorization assistance, according to an example embodiment of the invention.

FIG. 1 illustrates an example healthcare system 100 for facilitating claim rejection resolution by providing prior authorization assistance, according to an example embodiment of the invention. As shown in FIG. 1, the system 100 may include a pharmacy computer 103, a service provider computer 104, a claims processor computer 106, and a prior authorization assistance computer 108, which are each configured for accessing and reading associated computer-readable media having stored thereon data and/or computer-executable instructions for implementing the various methods of the invention. Generally, network devices and systems, including the one or more pharmacy computers 103, service provider computers 104, claims processor computers 106, and prior authorization assistance computers 108, have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" may describe any form of computer memory or memory device. It will be appreciated that each of the pharmacy computers 103, service provider computers 104, claims processor computers 106, or prior authorization assistance computer 108 may be associated with one or more computers, according to an example embodiment of the invention.

As shown in FIG. 1, the pharmacy computer 103, service provider computer 104, claims processor computer 106, and prior authorization assistance computer 108 may be in communication with each other, either directly or indirectly, via a network such as network 110, which as described below can include one or more separate or shared private and public networks, including the Internet or a publicly switched telephone network. Each of these components—the pharmacy computer 103, the service provider computer 104, the claims processor computer 106, the prior authorization assistance computer 108, and the network 110—will now be discussed in further detail.

First, the pharmacy computer 103 may be any processor-driven device, such as a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. In addition to having processor(s) 149, the pharmacy computer 103 may further include a memory 142, input/output ("I/O") interface(s) 154, and network interface(s) 156. The memory 142 may store data files 158 and various program modules, such as an operating system ("OS") 150, a client module 152, and a database management system ("DBMS") to facilitate management of data files 158 and other data stored in the memory 142 and/or stored in separate databases. The memory 142 may be any computer-readable medium, coupled to the processor(s) 149, such as RAM, ROM, and/or a removable storage device. The OS 150 may be, but is not limited to, Microsoft Windows®, Apple OSX™, Linux, Unix, or a mainframe operating system. The client module 152 may be an Internet browser or other software, including a dedicated program, for interacting with the service provider computer 104 and/or the claims processor computer 106. For example, a user 124 such as a pharmacist or other pharmacy employee may utilize the client module 152 in preparing and providing a healthcare (e.g., prescription) claim request to the service provider computer 104 for delivery to the appropriate claims processor computer 106 for adjudication or other coverage/benefits determination. In addition, the user 124 can use the client module 152 in preparing and providing a request for prior authorization, whether or not stylized in the form of a billing request/prescription claim request, to the service provider computer 104. Likewise, the pharmacy computer 103 may also utilize the client module 152 to retrieve or otherwise receive data, messages, or responses from the service provider computer 104, the claims processor computer 106, and/or the prior authorization assistance computer 108.

Second, the service provider computer 104 may include, but is not limited to, any processor-driven device that is configured for receiving, processing, and fulfilling requests from the pharmacy computer 103, the claims processor computer 106, and/or prior authorization assistance computer 108, relating to prescription, pharmacy, benefits, and/or healthcare transactions or other activities, including requests for prior authorization assistance. The service provider computer 104 may include, but is not limited to, a server computer, a mainframe computer, one or more networked computers, or any other processor-based device. According to an example embodiment of the invention, the service provider computer 104 may comprise, but is not limited to, one or more "switches" or "switch providers" performing routing and processing (e.g., pre- and post-routing editing) of transactions relating to prescription claims and/or prior authorization assistance requests between or among pharmacies, payors/claims processors, prior authorization assistance entities, and/or other service providers.

The service provider computer 104 may include processor(s) 126, a memory 128, input/output ("I/O") interface(s) 130, and network interface(s) 132. The memory 128 may be any computer-readable medium, coupled to the processor(s) 126, such as RAM, ROM, and/or a removable storage device for storing data files 134 and a database management system ("DBMS") 138 to facilitate management of data files 134 and other data stored in the memory 128 and/or stored in one or more databases 182. The memory 128 may also store various program modules such as an operating system ("OS") 136, and the host module 140. The OS 136 may be, but is not limited to, Microsoft Windows®, Apple OSX™, Linux, Unix, or a mainframe operating system.

The data files 134 may also store routing tables for determining the destination of communications received from pharmacy computer(s) 103 or claims processor computer(s) 106. The routing tables can also store destinations of available prior authorization assistance computer(s) 108. The host module 140 may receive, process, and respond to requests from the client module 152 of the pharmacy computer 103, and may further receive, process, and respond to requests from the host modules 172, 188 of respective claims processor computer 106 or prior authorization assistance computer 108. The database 182 may comprise one or more databases operable for storing information that supports facilitating claim resolution and/or the providing of prior authorization assistance, in accordance with an example embodiment of the invention. For example, the database 182 may store, perhaps in a history file or other similar list/record structure, transaction history records having information from one or more prescription claim transactions for which prior authorization assistance is eligible or for which prior authorization assistance has been facilitated, directed, or provided, according to an example embodiment of the invention.

A prior authorization assistance logic module 109 may also be operative with the service provider computer 104. The prior authorization assistance logic module 109 may include computer-executable instructions for facilitating claim rejection resolution and/or prior authorization assistance, as described herein. As an example, the prior authorization assistance logic module 109 may be operative to qualify prescription claim transactions for eligibility for prior authorization assistance, and/or generate or provide, either alone or in conjunction with service provider computer 104, a request for prior authorization assistance to a prior authorization assistance computer 108, as described herein. Where needed, the prior authorization assistance logic module 109 may store or record prescription claim transaction records in a history file or other similar list/record structure of the database 182 to support the facilitation of prior authorization assistance. For example, the prior authorization assistance logic module 109 may be operative to match a request for prior authorization assistance from pharmacy computer 103 to a stored transaction history record of a prior claim transaction in order to obtain information needed to generate a request for prior authorization assistance for delivery to the prior authorization assistance computer 108. In an example embodiment of the invention, the prior authorization assistance logic module 109 may be implemented as computer-implemented instructions of the memory 128 of the service provider computer 104. Alternatively, the prior authorization assistance logic module 109 may also be implemented as computer-implemented instructions of a memory of separate processor-based system, according to an example embodiment of the invention.

Third, the claims processor computer 106 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The claims processor computer 106 may include processor(s) 158, a memory 160, input/output ("I/O") interface(s) 162, and network interface(s) 164. The memory 160 may be any computer-readable medium, coupled to the processor 158, such as RAM, ROM, and/or a removable storage device for storing data files 166 and a database management system ("DBMS") to facilitate management of data files 166 and other data stored in the memory 160 and/or stored in separate databases. The memory 160 may also store various program modules, such as an operating system ("OS") 168 and a host module 172. The OS 168 may be, but is not limited to, Microsoft Windows®, Apple OSX™, Linux, Unix, or a mainframe operating system. The host module 172 may receive, process, and respond to requests from the client module 152 of the pharmacy computer 103, and may further receive, process, and respond to requests from the host module 140 of the service provider computer 104. According to an example embodiment of the invention, the claims processor computer 106 may be associated with coverage or benefits determination by a government payor, an insurance company, a pharmacy benefits manger (PBM), or another third-party payor. According to an alternative example embodiment of the invention, a claims processor computer 106 may also be implemented as part of a service provider computer 104 or may otherwise be affiliated with the service provider computer 104.

The prior authorization assistance computer 108 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. The prior authorization assistance computer 108 may include processor(s) 190, a memory 186, input/output ("I/O") interface(s) 192 and network interface(s) 194. The memory 186 may be any computer-readable medium, coupled to the processor 190, such as RAM, ROM, and/or a removable storage device for storing data files 182 and a database management system ("DBMS") to facilitate management of data files 182 and other data stored in the memory 186 and/or stored in separate databases. The memory 186 may also store various program modules, such as an operating system ("OS") 182 and a host module 172. The OS 182 may be, but is not limited to, Microsoft Windows®, Apple OSX™, Linux, Unix, or a mainframe operating system. The host module 188 may receive, process, and respond to requests from the host modules 140, 172 of the respective service provider computer 104 or claims processor computer 106, and may further receive, process, and respond to requests from the client module 152 of the pharmacy computer 103. For example, the host module 188 may receive requests for prior authorization assistance, and in response, may initiate a process for completing a prior authorization form and delivering the completed prior authorization form to one or more payors, as described herein. According to an example embodiment of the invention, the prior authorization assistance computer 108 may be associated with an entity that facilitates claim rejection resolution by providing prior authorization assistance, which may include the completion and delivery of prior authorization forms to one or more payors. According to an alternative example embodiment of the invention, the prior authorization assistance computer 108 may also be associated with the service provider associated with the service provider computer 104. In this alternative embodiment, the prior authorization assistance computer 108 may also be implemented as part of a service provider computer 104 or may otherwise be affiliated with the service provider computer 104.

The network 110 may include any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 110 may also allow for real-time, off-line, and/or batch transactions to be transmitted between or among the pharmacy computer 103, the service provider computer 104, the claims processor computer 106, and/or the prior authorization assistance computer 108. Due to network connectivity, various methodologies as described herein may be practiced in the context of distributed computing environments. Although the service provider computer 104 is shown for simplicity as being in communication with the pharmacy computer 103, the claims processor computer 106, and/or the prior authorization assistance computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment of the invention. For example, the service provider computer 104 may form the basis of network 110 that interconnects the pharmacy computer 103, the claims processor computer 106, and/or the prior authorization assistance computer 108.

The system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one example embodiment, the service provider computer 104 (or the pharmacy computer 103/claims processor computer 106) may be implemented as a specialized processing machine that includes hardware and/or software for performing the methods described herein. In addition, the processor and/or processing capabilities of the service provider computer 104 and/or the prior authorization assistance logic module 109, may be implemented as part of the pharmacy computer 103, the claims processor computer 106, and/or the prior authorization assistance computer 108, or any portion or combination thereof. Accordingly, embodiments of the invention should not be construed as being limited to any particular operating environment, system architecture, or device configuration.

Operational Overview

Figure 2:
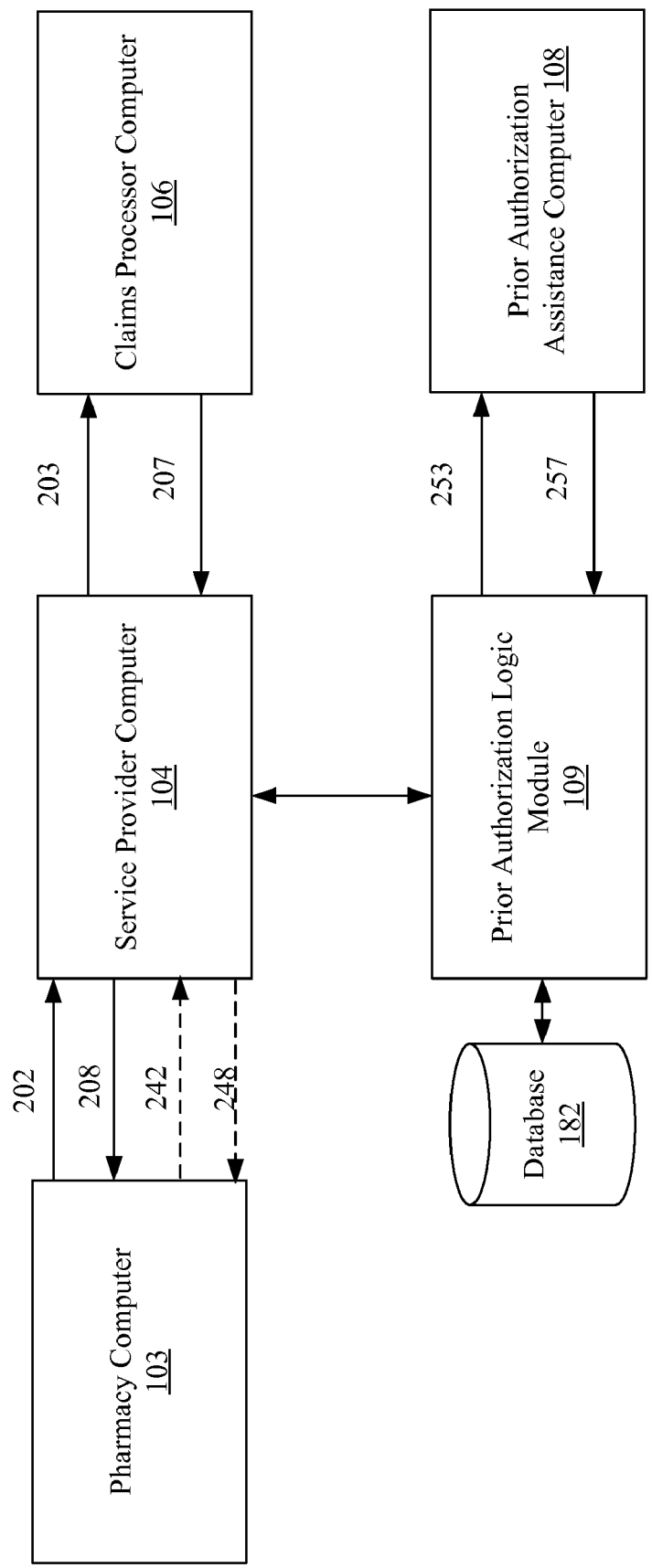
FIG. 2 illustrates an example block diagram for facilitating claim rejection resolution by providing prior authorization assistance, according to an example embodiment of the invention.

FIG. 2 illustrates an example block diagram for facilitating claim rejection resolution by providing prior authorization assistance, according to an example embodiment of the invention. The block diagram of FIG. 2 will be discussed in conjunction with the flow diagram 300 of FIG. 3. It will be appreciated that the flow diagram 300 of FIG. 3 may be performed either in whole or in part by a service provider computer 104, either operating alone or in conjunction with the prior authorization logic module 109, according to an example embodiment of the invention.

Figure 3:
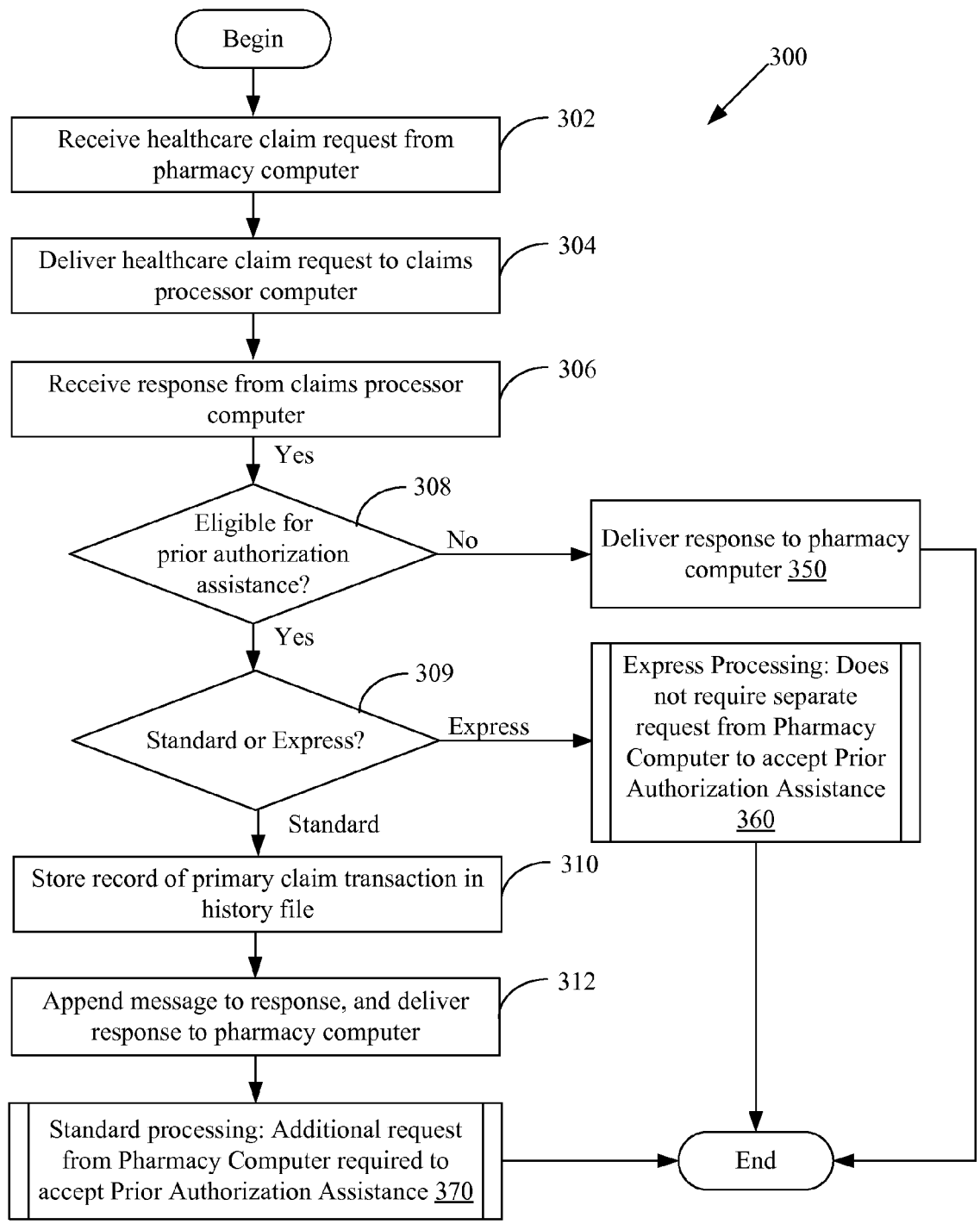
FIG. 3 illustrates an example flow diagram for facilitating claim rejection resolution by providing prior authorization assistance, according to an example embodiment of the invention.

Turning now to block 302 of FIG. 3, a pharmacy computer 103 may submit a prescription claim request 202 to the service provider computer 104. Accordingly, the service provider computer 104 may receive the prescription claim request 202 at block 302. According to an example embodiment of the invention, the prescription claim request 202 may be in accordance with a version of an NCPDP Telecommunication Standard, although other standards (e.g., Electronic Data Interchange (EDI)) may be utilized as well. The prescription claim request 202 may include a BIN Number and/or a Processor Control Number (PCN) for identifying a particular claims processor computer 106 as the destination. In addition, the prescription claim request 202 may also include information relating to the patient, payor, prescriber, pharmacy, and/or the prescribed drug or product. As an example, the prescription claim request 202 received by the service provider computer 104 may include one or more of the following information:

Payor ID/Routing Information
BIN Number (i.e. Banking Identification Number) or combination of a BIN Number and Processor Control Number (PCN), that designates a destination of the prescription claim request 202
Patient Information
Name (e.g., Patient Last Name, Patient First Name, etc.)
Date of Birth (DOB) (or age of patient)
Patient Gender Code (e.g., M=Male, F=Female)
Patient Address (e.g., Street Address, Zip Code, etc.)
Patient Contact Information (e.g., Telephone Number, Email Address, Fax Number, etc.)
Patient ID or other identifier
Insurance/Coverage Information
Cardholder Name (e.g., Cardholder First Name, Cardholder Last Name)
Cardholder ID and/or other identifier (e.g., person code)
Healthcare Provider Information
Prescriber Information
Primary Care Provider ID or other identifier (e.g., NPI code)
Primary Care Provider Name (e.g., Last Name, First Name)
Prescriber ID or other identifier (e.g., NPI code, DEA number)
Prescriber Name (e.g., Last Name, First Name)
Prescriber Contact Information (e.g., Telephone Number, Email Address, Fax Number, etc.)
Pharmacy/Pharmacist Provider Information
Pharmacy/Pharmacist ID (e.g., National Provider Identifier (NPI) code)
Pharmacy/Pharmacist Contact Information (e.g., Telephone Number, Email Address, Fax Number, etc.)
Claim Information
Drug or product information (e.g., National Drug Code (NDC))
Prescription/Service Reference Number
Date Prescription Written
Quantity Dispensed
Number of Days Supply
Diagnosis/Condition
Pricing information for the drug or product (e.g., network price, Usual & Customary price)
Date of Service.

It will be appreciated that an example prescription claim request 202 can include additional or alternative information from that illustrated above. Furthermore, it will be appreciated that many of the informational fields described above may be optional, or may otherwise vary depending upon requirements of the intended payor/claims processor computer 106 that will be adjudicating the prescription claim request.

At block 304, the service provider computer 104 may receive the prescription claim request 202. The service provider computer 104 may then route or deliver a copy of prescription claim request 202 to the destination claims processor computer 106 as prescription claim request 203 for coverage/benefits determination or other adjudication by the claims processor computer 106 associated with a payor. Where the claims processor computer 106 is part of the service provider computer 104 or otherwise affiliated with the service provider computer 104, the delivery of the prescription claim request 203 may be an internal delivery or an intra-network delivery. However, where the claims processor computer 106 is a processor-based system distinct from the service provider computer 104, the delivery of the prescription claim request 203 may be an external delivery, perhaps via a network 110, according to an example embodiment of the invention.

At block 306, the claims processor computer 106 may adjudicate the prescription claim request 203 and generate a claim response 207. The claim response 207 may indicate an approval of coverage and include financial coverage information that specifies a payor-covered amount (e.g., an insured amount) and a patient-responsible amount (e.g., a co-pay or coinsurance amount). Alternatively, the claim response 207 may indicate a denial of coverage for the prescription claim 203, which indicates no coverage by a payor. For a denial of coverage, the claim response 207 may include one or more denial reasons or reject codes. As an example, in accordance with an NCPDP Telecommunication Standard, an example reject code may be one or more of the following codes: (i) Reject Code="70" (Product/Service not covered), (ii) Reject Code="75" (Prior Authorization Required), or (iii) Reject Code="76" (Plan Limitation Exceeded). Many other possible reject codes are available without departing from example embodiments of the invention.

Following block 306 is block 308. At block 308, the service provider computer 104 may determine whether the present prescription claim transaction is eligible for prior authorization assistance. To do so, the service provider computer 104 may deliver at least a portion of the information from the prescription claim transaction (comprising the prescription claim request 202 and the claim response 207) to the prior authorization logic module 109. The received prescription claim transaction information is then analyzed by the prior authorization logic module 109 to determine whether the present prescription claim transaction is eligible for prior authorization assistance. An example implementation for block 308 will now be described with respect to the example flow diagram 400 of FIG. 4. It will be appreciated that portions or variations of FIG. 4 can be utilized as an example implementation for block 308, Turning now to FIG. 4, at block 402, the prior authorization assistance logic module 109 may determine whether the prescription claim transaction involves an eligible pharmacy. For example, block 404 may determine an eligible pharmacy by obtaining the pharmacy ID (or pharmacy name) from the prescription claim request 202, and then determining whether the pharmacy ID (or pharmacy name) matches a corresponding entry in a list of eligible pharmacy IDs (or pharmacy names). To be included on the list, a pharmacy may have previously registered with a service provider for prior authorization assistance, according to an example embodiment of the invention. If block 402 determines that the pharmacy is not an eligible pharmacy, then processing may proceed to block 409, where a determination is made that the prescription claim transaction is not eligible for prior authorization assistance. On the other hand, if block 402 determines that the pharmacy is an eligible pharmacy, then processing may proceed to block 404.

At block 404, the prior authorization assistance logic module 109 may determine whether the prescription claim transaction involves an eligible transaction type. For example, block 404 may determine an eligible transaction type based upon the prescription claim request 202 being of a "billing" type (e.g., Transaction code=B1). For a billing type transaction, block 404 may optionally determine an eligible transaction type by requiring that the prescription claim request 202 be a primary claim transaction, as opposed to a secondary claim transaction or coordination of benefits (COB) claim transaction. For example, block 404 may determine that the prescription claim request 202 is a primary claim request based upon the included Other Coverage Code (OCC) being of a particular value. If block 404 determines that the transaction type is not an eligible transaction type, then processing may proceed to block 409, where a determination is made that the prescription claim transaction is not eligible for prior authorization assistance. On the other hand, if block 404 determines that the transaction type is eligible, then processing may proceed to block 406.

At block 406, the prior authorization assistance logic module 109 may determine whether the prescription claim transaction was rejected. Block 406 may include the prior authorization assistance logic module 109 analyzing the claim response 207 to determine whether the prescription claim transaction (e.g., request 203) was rejected. If block 406 determines that the prescription claim was not rejected (e.g., otherwise, approved), then processing may proceed to block 409, where a determination is made that the prescription claim transaction is not eligible for prior authorization assistance. On the other hand, if block 406 determines that the prescription claim was rejected, then processing may proceed to block 408.

At block 408, the prior authorization assistance logic module 109 may determine whether the rejection of the prescription claim was based upon an eligible rejection code or rejection reason. Block 408 may include the prior authorization assistance logic module 109 analyzing the rejection code or rejection reason of the claim response 207 to determine whether it is an eligible reject code or rejection reason. For example, an eligible reject code or reason may include any of the following: (i) Reject Code="70" (Product/Service not covered), (ii) Reject Code="75" (Prior Authorization Required), or (iii) Reject Code="76" (Plan Limitation Exceeded). If block 408 determines that the reject code or reason of the claim response 207 is not an eligible reject code or reason, then processing may proceed to block 409, where a determination is made that the prescription claim transaction is not eligible for prior authorization assistance. On the other hand, if block 406 determines that the reject code or reason of the claim response 207 is an eligible reject code or reason, then processing may proceed to block 410.

At block 410, the prior authorization assistance logic module 109 may determine whether the drug or product identified in the prescription claim request 202 (e.g., by NDC number or drug/product name) is an eligible drug or product for prior authorization assistance. For example, an eligible drug or product may be determined by comparing an NDC number (or name of drug) of the prescription claim request 202 with a listing of eligible NDC numbers (or names of drugs). If block 410 determines that the drug or product identified by the prescription claim request 202 is not eligible, then processing may proceed to block 409, where a determination is made that the prescription claim transaction is not eligible for prior authorization assistance. On the other hand, if block 404 determines that the drug or product is eligible, then processing may proceed to block 412, where a determination that the prescription claim transaction is eligible for prior authorization assistance.

Figure 4:
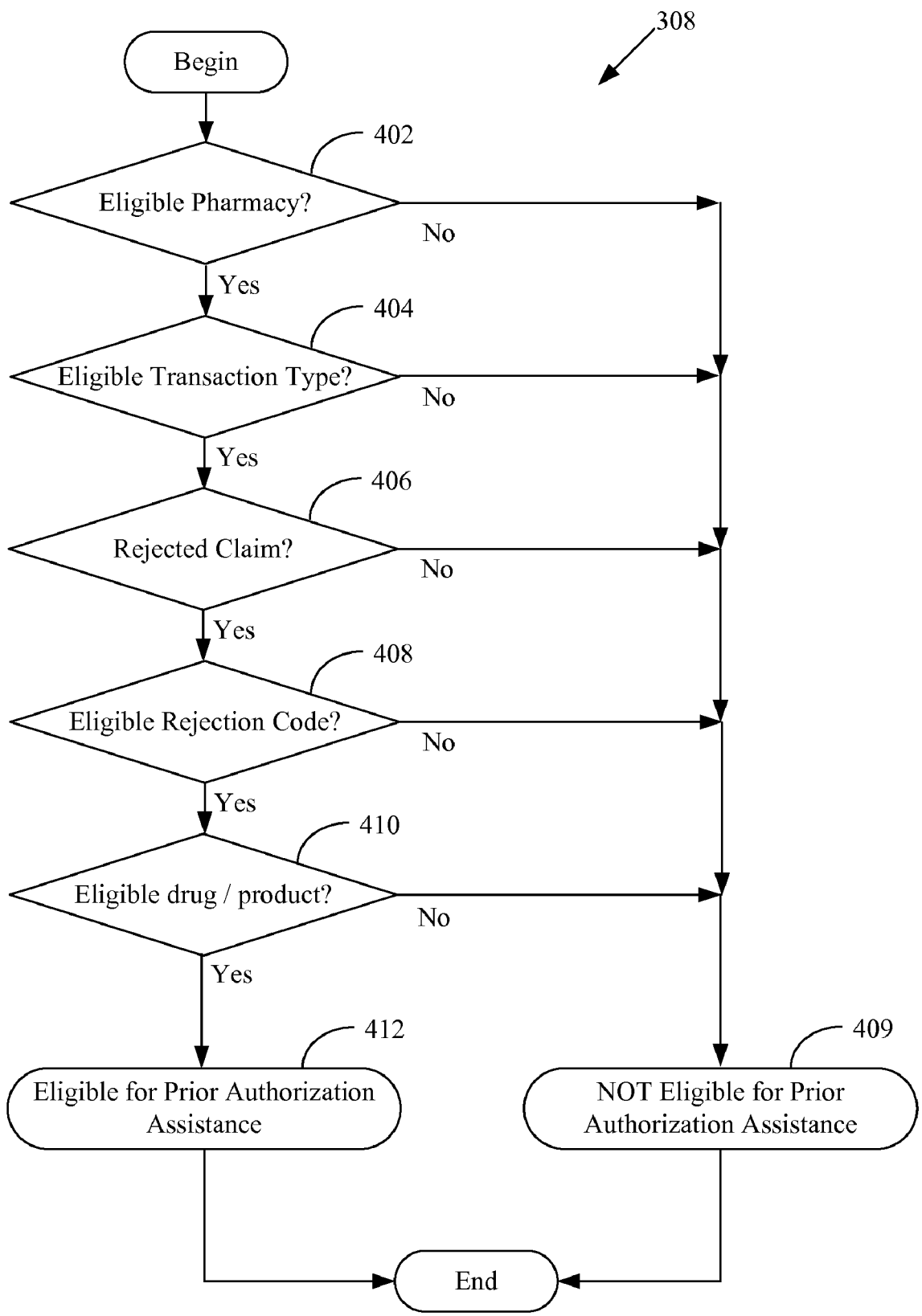
FIG. 4 illustrates an example flow diagram for determining whether a claim transaction is eligible for prior authorization assistance, according to an example embodiment of the invention.

It will be appreciated that example variations of FIG. 4 (and block 308 of FIG. 3) are available in accordance with an example embodiment of the invention. For example, one or more blocks of FIG. 4 may be omitted or varied. As another example, while FIG. 4 (and block 308 of FIG. 3) has been illustrated as a post-adjudication step, it will be appreciated that one or more blocks of FIG. 4 may also be performed as a pre-adjudication step. For example, with reference to FIG. 4, blocks 402, 404, 410 may be performed as a pre-adjudication step prior to the prescription claim request 202 being routed by the service provider computer 104 to the claims processor computer 106 as prescription claim request 203. On the other hand, blocks 406, 408 may remain a post-adjudication step that occurs after the claims processor computer 106 delivers the claim response 207 to the service provider computer 104/prior authorization assistance logic module 109.

Once the processing of FIG. 4 completes, then a determination will be available at block 308 of FIG. 3 for whether the present prescription claim transaction is eligible for prior authorization assistance. Returning now to block 308, if the prescription claim transaction is not eligible for prior authorization assistance, then prior authorization logic module 109 may provide a response to service provider computer 104 to indicate the lack of eligibility for prior authorization assistance, and processing may proceed to block 350. At block 350, the service provider computer 104 may provide a claim response 208 to the pharmacy computer 103. The claim response 208 may be a copy of the claim response 207, or at least a portion thereof, generated by the claims processor computer 106, according to an example embodiment of the invention.

On the other hand, block 308 may determine that the prescription claim transaction is eligible for prior authorization assistance, and processing may proceed to block 309. At block 309, the prior authorization logic module 109 may determine whether standard handling or express handling of prior authorization assistance should be utilized. In an example embodiment of the invention, standard handling may require that a pharmacy affirmatively request prior authorization assistance by having the pharmacy computer 103 deliver a subsequent request for prior authorization assistance (e.g., request 242) to the service provider computer 104, as described herein. On the other hand, express handling may not require any additional request from the pharmacy computer 103 prior to engaging the services of a prior authorization assistance entity. The determination in at block 308 between standard or express handling may be based at least in part on previously stored preferences of the pharmacy associated with the prescription claim transaction. Accordingly, a pharmacy's preference may be determined by utilizing the Pharmacy ID or pharmacy name from the request 202 and identifying whether a corresponding preference for standard or express processing has been previously stored, perhaps in database 182. If no preference has been identified or stored, then a default processing may be standard processing, or alternatively express processing, according to an example embodiment of the invention. In addition, even if a pharmacy has specified a preference for express processing, block 309 may further determine whether any additional requirement for express processing is met. For example, express processing may additionally require that certain required information is available from the prescription claim transaction (request 202 and/or response 207) in order to generate a request 253 for prior authorization assistance for delivery to prior authorization assistance computer 108. It will be appreciated that the required information for generating the request 253 for prior authorization assistance may be the same regardless of the payor/claims processor computer 106 involved in the claim transaction, or it may differ based upon the associated payor/claims processor computer 106.

Figure 5:
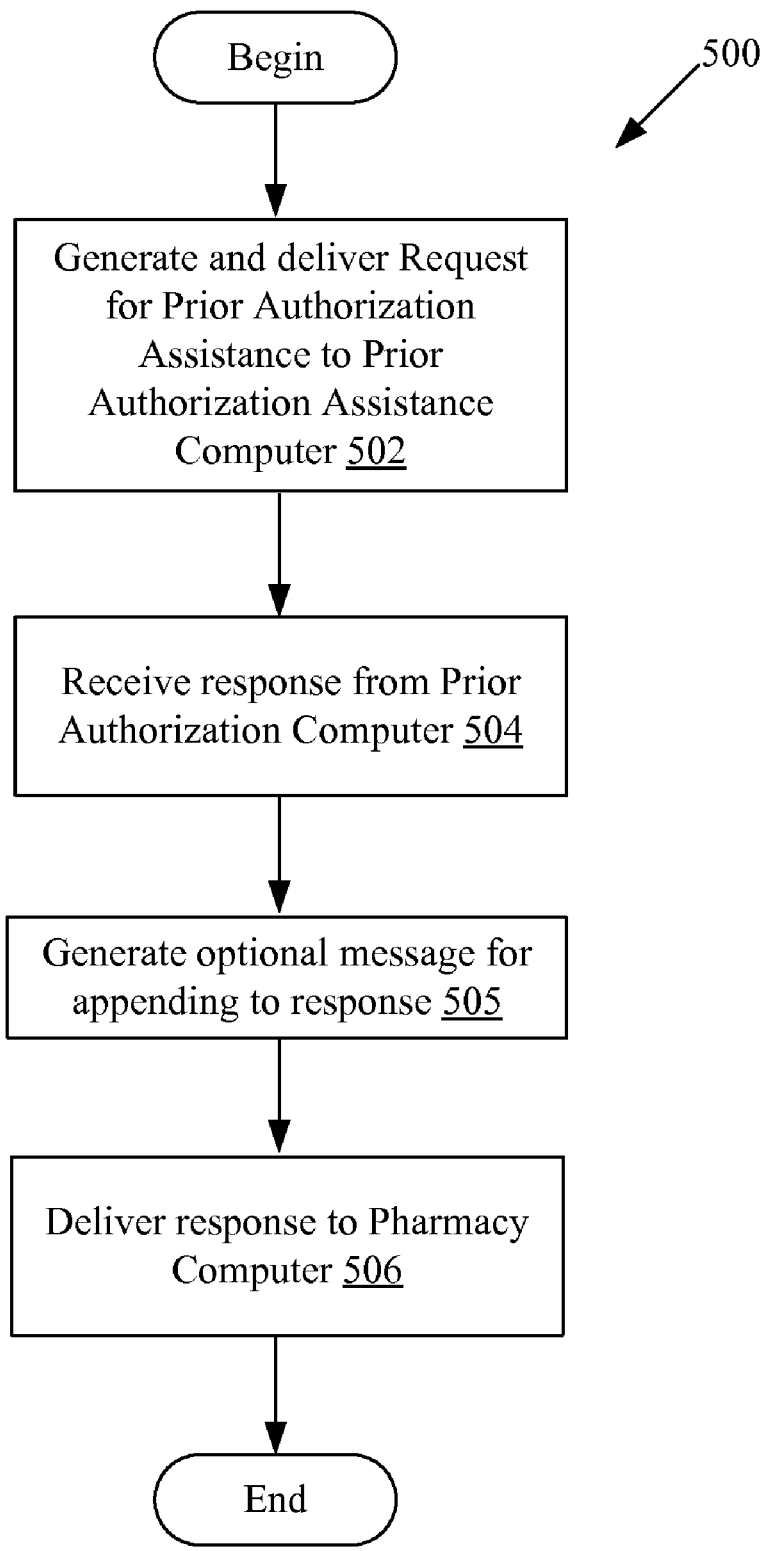
FIG. 5 illustrates a flow diagram of an example process that does not utilize an additional request for prior authorization assistance, according to an example embodiment of the invention.

If the requirements for express processing are met at block 309, then processing may proceed to block 360 for the express processing. An example implementation for the express processing in block 360 is illustrated by the example flow diagram 500 of FIG. 5, although many variations are available without departing from example embodiments of the invention. Turning now to FIG. 5, at block 502, the prior authorization logic module 109 and/or service provider computer 104 can generate a request 253 for prior authorization assistance. The information included in the request 253 can generally include one or more combinations of the following information:

Payor ID: Identification (e.g., name, BIN or BIN/PCN combination) of the payor/claims processor computer 106 that rejected the prescription claim request.
Patient Information
    Name (e.g., Patient Last Name, Patient First Name, etc.)
    Patient Address (e.g., Street Address, Zip Code, etc.)
    Patient Date of Birth (DOB) (or age of patient)
    Patient Gender Code
    Patient Contact Information (e.g., Patient Telephone Number)
    Patient ID or other identifier
Insurance/Coverage Information
    Cardholder Name (e.g., Cardholder First Name, Cardholder Last Name)
    Cardholder ID and/or other identifier (e.g., person code)
Healthcare Provider Information
    Prescriber ID or other identifier (e.g., NPI code, DEA number)
    Prescriber Name (e.g., Last Name, First Name)
    Prescriber Contact Information (e.g., telephone number, fax number, email address)
    Pharmacy/Pharmacist Information
    Pharmacy/Pharmacist ID (e.g., National Provider Identifier (NPI) code)
    Pharmacy/Pharmacist Contact Information (e.g., telephone number, fax number, email address)
Claim Information
    Reject Code (e.g., 75=Prior Authorization Required)
    Drug or product information (e.g., National Drug Code (NDC))
    Prescription/Service Reference Number
    Date Prescription Written
    Quantity Dispensed
    Number of Days Supply
    Diagnosis/Condition
    Pricing information for the drug or product (e.g., network price, Usual & Customary price)
Date of Service.

The information included in the request 253 may be obtained from the prescription claim transaction, including the prescription claim request 202 and the claim response 203. In some example embodiments, the information included in the request 253 can be derived or obtained from other sources as well. For example, healthcare provider information, including addresses and contact information, can be obtained from a healthcare provider database or listing that includes the addresses and contact information for various healthcare providers. Accordingly, an identifier such as a prescriber ID or a pharmacy/pharmacist ID from the prescription claim transaction can be used to obtain additional information from a healthcare provider database. Generally, information included in the prescription claim transaction can be used to obtain or derive additional information from a variety of internal or external sources to the service provider computer 104 and/or the prior authorization logic module 109, according to an example embodiment of the invention.

The request 253 for prior authorization assistance can be embodied in a variety of electronic formats, including EDI formats, according to an example embodiment of the invention. In an example embodiment of the invention, the request 253 for prior authorization assistance can be stylized as a billing transaction, such as that provided in a version of the NCPDP Telecommunication Standard, notwithstanding that billing transactions (e.g., such as that for claim request 202) are conventionally utilized for requesting financial reimbursement from payors such as insurance companies, PBMs, private payors, government payors, etc. To modify a billing transaction for use as the request 253 for prior authorization assistance, the billing transaction may include a particular identifier such a unique BIN Number or BIN Number/PCN combination, either alone or in combination with one or more other fields (e.g., Group ID) in a billing transaction, that can designate or indicate an association with a particular prior authorization assistance entity or prior authorization assistance computer 108. At block 502, the generated request 253 for prior authorization assistance can then be delivered by the prior authorization logic module 109 and/or service provider computer 104 to the prior authorization assistance computer 108. At block 504, the prior authorization logic module 109 and/or service provider computer 104 may optionally receive a response 257 from the service provider computer 104, where the response 257 may indicate successful receipt and/or validation of the request 253. Alternatively, the response 257 may indicate that one or more required fields are missing or erroneous, in which case, the prior authorization logic module 109 and/or service provider computer 104 may correct the errors and resubmit another request 253 to the prior authorization assistance computer 108.

Following block 504 is block 505, where one or more messages can be generated for appending to any response delivered according to block 506 below. According to an embodiment, the message can indicate that the request 253 was not accepted by the prior authorization assistance computer 108, and may further identify one or more reasons for the non-acceptance. Alternatively, the message that the request 253 has been accepted by or delivered to a prior authorization assistance computer 108. The message can also instruct the pharmacy to resubmit a claim request 202 in X days or Y hours when the prior authorization assistance process is expected to have been completed (e.g., prior authorization for a drug/product for a patient approved by a payor). An example message may be: "Prior Authorization Request Accepted. Resubmit prescription billing request in 48 hours. Call 1-XXX-XXX-XXXX (if any questions remain."

Following block 505 is block 506. At block 506, the service provider can generate a claim response 208, which may incorporate or append any messages (e.g., in a free-text message field) generated at block 505. The claim response 208 may be responsive to the prescription claim request 202. The claim response 208 may also include information (e.g., reject code, etc.) from the claim response 203 received from claim processor computer 106, according to an example embodiment of the invention. In addition, it will be appreciated that the response 208 may be further be stylized as either a "rejection" or "approval" based upon preferences of the pharmacy associated with the pharmacy computer 103. For example, if the pharmacy prefers a rejection, then the response 208 may be indicated as "rejected" and the rejection reason/code can be the same as the one from response 203 from the claims processor computer 106. Alternatively, another rejection reason/code can be specified to indicate the provisioning of prior authorization assistance. On the other hand, if the pharmacy prefers an approval, then the response 208 may be indicated as an "approved". However, since the payor/claims processor computer 106 denied coverage, the patient responsibility amount (e.g., co-pay amount and/or co-insurance amount) may be indicated as 100% of the price of the drug or product (e.g., full price or a retail price of the drug or product). The ability of a pharmacy to specify preferences for receiving an "approved" or "rejected" claim can allow pharmacy management software on the pharmacy computer 103 to properly queue or manage certain claim transactions for appropriate follow-up (e.g., submission of additional claims once the prior authorization assistance process is complete). It will be appreciated that the pharmacy preferences for receiving an "approved" or "rejected" claim may have been received when a pharmacy enrolled or registered to participate in a prior authorization assistance program, and the preferences may have been stored in association with a pharmacy name or pharmacy ID for later use or retrieval, perhaps from database 182 or another memory location.

Returning back to FIG. 3, block 309 could otherwise determine that standard processing is to be performed instead of express processing, and processing may proceed to block 310. At block 310, the service provider computer 104 and/or prior authorization assistance logic module 109 may store or direct the storage of a transaction history record of the prescription claim transaction in a history file or other list/record structure in the database 182, according to an example embodiment of the invention. An example transaction history record in the history file or similar list/record structure may include some or all of the following information:

Payor ID: A name or BIN Number/PCN that is associated with a payor,

Patient ID: An identifier for the patient such as the cardholder ID and/or group ID, or patient name, Drug/Product ID: an identifier of the drug or product, such as the NDC number, Pharmacy ID: an identifier of the pharmacy/pharmacy computer 102 originating the claim request, Quantity Dispensed: a dispensing quantity for the drug or product, Prescription (Rx)/Service Number, and/or Date of Service: a date identifying when the prescription was requested to be filled.

It will be appreciated that additional information from the prescription claim transaction can be stored with the transaction history record in the history file or similar list/record structure without departing from example embodiments of the invention. It will also be appreciated that a record may be maintained in the history file or list/record structure for only a limited period of time. For example, the history file or list/record structure may only maintain records in which the associated date of service is within a particular time period (e.g., 7 days, 14 days, etc.). In this way, records in the history file or list/record structure may be automatically purged or replaced on a periodic basis. It will also be appreciated that while the history file or similar list/record may be captured during operation of the service provider computer 104, the records could also be uploaded into the database 182 from an external source, including another service provider or data provider.

Following block 310, processing may proceed to block 312. At block 312, the service provider computer 104 can generate a claim response 208, which may be responsive to the prescription claim request 202. The claim response 208 may be a copy of the claim response 203, or otherwise include information from the claim response 203 according to an example embodiment of the invention. In addition, the claim response 208 can include a message (e.g., in a message field) indicating that prior authorization assistance may be available with instructions on how to request prior authorization assistance. An example message can include: "Prior Authorization Assistance Available-Submit Primary Claim or Coordination of Benefits (COB) Claim to BIN Number XXXXX" At block 312, the claim response 208 can then be delivered from the service provider computer 104 to the pharmacy computer 103.

Following block 312, processing may proceed to block 370 for the standard processing that may occur if a pharmacy wishes to take advantage of the offer for prior authorization assistance.

Figure 6:
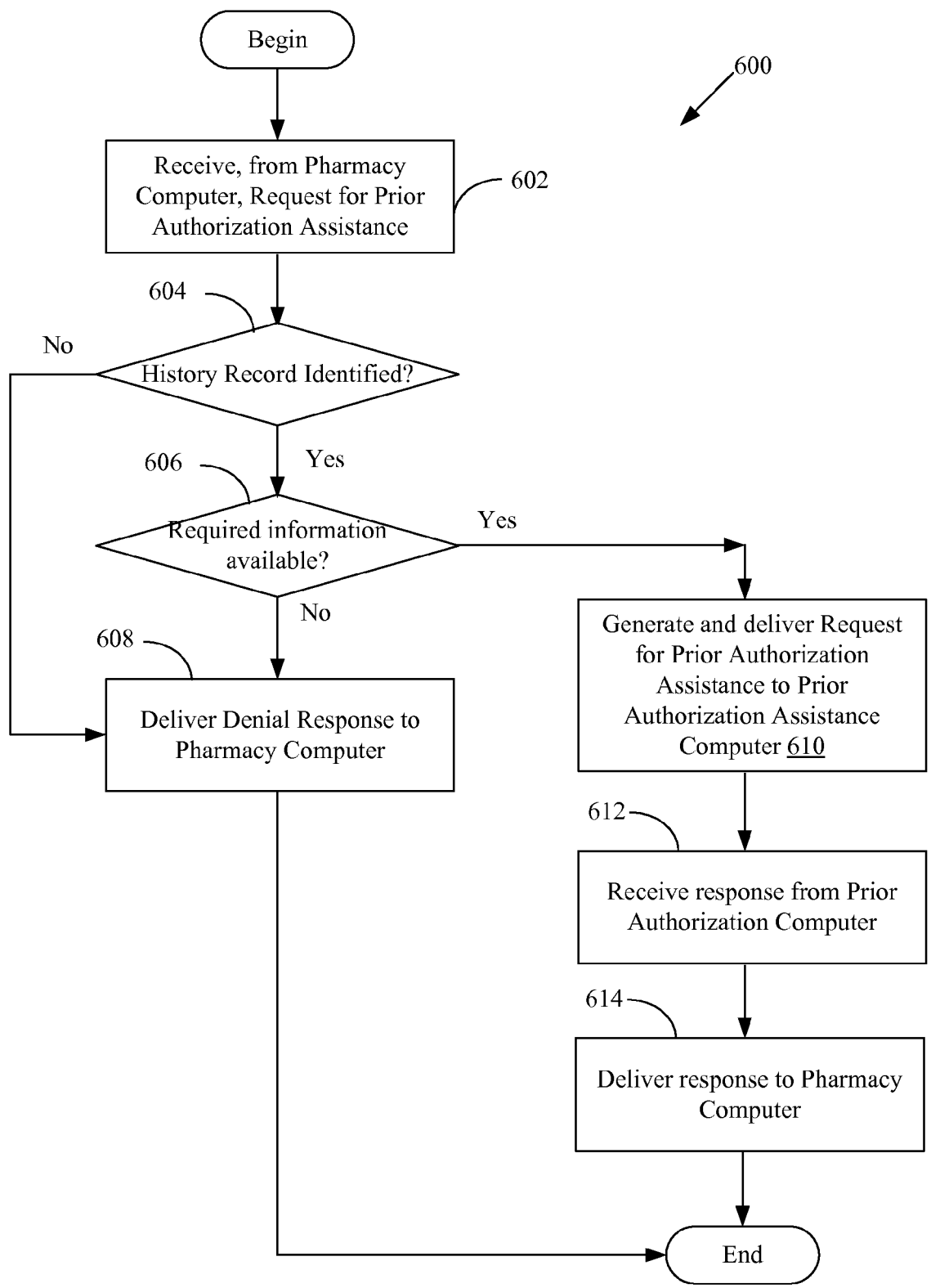
FIG. 6 illustrates a flow diagram of an example process that utilizes an additional request for prior authorization assistance, according to an example embodiment of the invention.

An example implementation for the standard processing in block 370 is illustrated by the example flow diagram 600 of FIG. 6, although many variations are available without departing from example embodiments of the invention. Turning now to FIG. 6, at block 602, the service provider computer 103 may receive a request 242 for prior authorization assistance. The request 242 for prior authorization assistance can be stylized as a billing transaction, such as that provided in a version of the NCPDP Telecommunication Standard, notwithstanding that billing transactions (e.g., such as that for claim request 202) are conventionally utilized for requesting financial reimbursement from payors. As a billing transaction, the request 242 can further be stylized as a primary claim request or a coordination of benefits (COB) claim request (e.g., related to the prior claim request 202), according to an example embodiment of the invention. To modify a billing transaction for use as the request 242 for prior authorization assistance, the billing transaction may include a particular identifier such a unique BIN Number or BIN Number/PCN combination, either alone or in combination with one or more other fields (e.g., Group ID) in a billing transaction, that can designate or indicate an association with a particular prior authorization assistance entity or prior authorization assistance computer 108. The use of a particular BIN Number or BIN Number/PCN combination may also allow the pharmacy management software of the pharmacy computer 103 to track those rejected prescription claim transactions for which prior authorization assistance has been requested. The request 242 for prior authorization assistance can also include information utilized for matching to a previously stored transaction history record of the corresponding prior prescription claim transaction in a history file or other list/record structure in the database 182, according to an example embodiment of the invention. As such, the request 242 for prior authorization assistance may including the following information:

An identifier of the payor/claims processor computer 106 (e.g., name, BIN Number/PCN) that rejected the prior prescription claim request 203;

Prescription (Rx)/Service Number associated with the prior prescription claim transaction;

Identifier of the pharmacy/pharmacy computer 102 originating the prior prescription claim request 202, Identifier of Drug/Product (e.g., NDC number) that was the subject of the prior prescription claim transaction.

Date of Service associated with the prior prescription claim transaction.

In addition, the request 242 for prior authorization assistance can further include additional information associated with the patient, payor (e.g., insurer), or healthcare provider (e.g., prescriber, pharmacist, etc.). It will be appreciated that any additional information required may be based upon what information was already provided in the prior prescription claim request 202 and further based upon requirements of the service provider computer 104 and/or prior authorization assistance computer 108. For example, the service provider computer 104 and/or prior authorization assistance computer 108 may specify the required information, which may be the same or different depending upon the payor involved. Accordingly, a first portion of the required information may have been provided in the claim transaction request 202, and a second portion of the required information may be provided in the request 242, where the first and second portions collectively provide at least the required information. The request 242 for prior authorization assistance may be delivered by the service provider computer 104 to the prior authorization logic module 109.

At block 604, the service provider computer 104 and/or prior authorization logic module 109 may determine whether a prior transaction history record of the prior rejected prescription claim transaction can be located in a history file or other list/record structure in the database 182, according to an example embodiment of the invention. To do so, the service provider computer 104 and/or prior authorization logic module 109 may attempt to locate the history record by matching based upon corresponding information included in or derived from the request 242. The information used for matching may include one or more combinations of the following (i) an identifier of the payor/claims processor computer 106 (e.g., name, BIN Number/PCN) that rejected the prior prescription claim request 203, (ii) a Prescription (Rx)/Service Reference Number associated with the prior prescription claim transaction, (iii) an identifier of the pharmacy/pharmacy computer 102 originating the prior prescription claim request 202, (iv) an identifier of the Drug/Product (e.g., NDC number) that was the subject of the prior prescription claim transaction, and/or (v) Date of Service associated with the prior prescription claim transaction.

If block 604 determines that a transaction history record cannot be identified, then the prior authorization logic module 109 can provide a response to the service provider computer 104 that no history record corresponding to a prior rejected prescription claim transaction could be identified, and processing may proceed to block 608. At block 608, the service provider computer 104 provides a response 248 to the request 242, where the response 248 indicates that the request 242 for prior authorization assistance was denied or otherwise could not be completed. Optionally, the response 248 may indicate a reason for the denial, including the lack of identification of a transaction history record.

On the other hand, block 604 may identify a transaction history record for the prior rejected prescription transaction, in which case processing may proceed to block 606. At block 606, the prior authorization logic module 109 may determine whether it has access to all of the required information to generate and deliver a request 253 for prior authorization assistance to the prior authorization computer 108. The required information for the request 253 may be obtained from the request 242 and/or the identified stored transaction history record for the prior rejected prescription transaction. As an example, the stored transaction history record may provide all required information except for the patient's address and contact information, which missing items may be obtained from the request 242, according to an example embodiment of the invention. Likewise, additional information can be derived or obtained from other sources as well (e.g., healthcare provider databases), as described herein. The required information for generating the request 253 for prior authorization assistance may be the same regardless of the payor/claims processor computer 106 involved in the claim transaction, or may differ based upon the associated payor/claims processor computer 106, according to an example embodiment of the invention.

If block 606 determines that the required information for generating the request 253 is not available, then processing may proceed to block 608. At block 608, the service provider computer 104 provides a response 248 to the request 242, where the response 248 indicates that the request 242 for prior authorization assistance was denied or otherwise could not be completed. Optionally, the response 248 may indicate a reason for the denial, including the lack of certain required information.

On the other hand, if block 606 determines that the required information for generating the request 253 is available, then processing may proceed to block 610. At block 610, the prior authorization logic module 109 and/or service provider computer 104 can generate a request 253 for prior authorization assistance. The request 253 can include one or more combinations of payor information, patient information, insurance/coverage information, healthcare provider information, claim information, and date of service, as previously described herein. The information included in the request 253 may be obtained from the request 242 and/or the identified stored transaction history record. In some example embodiments, the information included in the request 253 can be derived or obtained from other sources as well. Generally, information included in the request 242 and/or stored transaction history record can be used to obtain or derive additional information from a variety of internal or external sources to the service provider computer 104 and/or the prior authorization logic module 109, according to an example embodiment of the invention.

As also described herein, the request 253 for prior authorization assistance can be embodied in a variety of electronic formats, including EDI formats, according to an example embodiment of the invention. In an example embodiment of the invention, the request 253 for prior authorization assistance can be stylized as a billing transaction, such as that provided in a version of the NCPDP Telecommunication Standard, notwithstanding that billing transactions (e.g., such as that for claim request 202) are conventionally utilized for requesting financial reimbursement from payors such as insurance companies, PBMs, private payors, government payors, etc. The request 253 can include a particular identifier such a unique BIN Number or BIN Number/PCN combination, either alone or in combination with one or more other fields (e.g., Group ID) in a billing transaction, that can designate or indicate an association with a particular prior authorization assistance entity or prior authorization assistance computer 108. It will be appreciated that the BIN Number or BIN Number/PCN combination in the request 253 may be the same as the one provided in the request 242, according to an example embodiment of the invention. At block 610, the generated request 253 for prior authorization assistance can then be delivered by the prior authorization logic module 109 and/or service provider computer 104 to the prior authorization assistance computer 108.

Following block 610 is block 612. At block 612, the prior authorization logic module 109 and/or service provider computer 104 may optionally receive a response 257 from the service provider computer 104, where the response 257 may indicate successful receipt and/or validation of the request 253. Alternatively, the response 257 may indicate that one or more required fields are missing or erroneous, in which case, the prior authorization logic module 109 and/or service provider computer 104 may correct the errors and resubmit another request 253 to the prior authorization assistance computer 108.

Following block 612 is block 614. At block 614, the service provider computer 104 can generate a response 248, which may be responsive to the request 248. The response 248 may include a message that a request 253 for prior authorization assistance has been accepted by a prior authorization assistance computer 108. The response 248 may also include a message requesting that the pharmacy resubmit a claim request 202 in X days or Y hours when the prior authorization assistance process is expected to have been completed. An example message may be: "Prior Authorization Request Accepted. Resubmit prescription billing request in 48 hours. Call 1-XXX-XXX-XXXX if any questions remain."

Where the request 242 is stylized as a billing transaction request, the response 248 may be further be stylized as either a "rejection" or "approval" based upon preferences of the pharmacy associated with the pharmacy computer 103. For example, if the pharmacy prefers a rejection, then the response 248 may be indicated as "rejected" and the rejection reason/code can be the same as the one specified in the stored transaction history record. Alternatively, another rejection reason/code can be specified to indicate the provisioning of prior authorization assistance. On the other hand, if the pharmacy prefers an approval, then the response 248 may be indicated as an "approved". However, since the payor/claims processor computer 106 previously denied coverage, the patient responsibility amount (e.g., co-pay amount and/or co-insurance amount) may be indicated as 100% of the price of the drug (e.g., full price or retail price). The ability of a pharmacy to specify preferences for receiving an "approved" or "rejected" claim can allow pharmacy management software on the pharmacy computer 103 to properly queue or manage certain claim transactions for appropriate follow-up (e.g., submission of additional claims once the prior authorization assistance process is complete). It will be appreciated that the pharmacy preferences for receiving an "approved" or "rejected" claim may have been received when a pharmacy enrolled or registered to participate in a prior authorization assistance program, and the preferences may have been stored in association with a pharmacy name or pharmacy ID for later use or retrieval, perhaps from database 182 or another memory location.

It will be appreciated that many variations of FIGS. 3-6 are available without departing from example embodiments of the invention. For example, while the request 253 is illustrates as being delivered from the prior authorization logic module 109 and/or the service provider computer 104 to the prior authorization assistance computer 108 on a real-time basis, the request 253 could also be batched with other similar requests and provided to the prior authorization assistance computer 108 on a periodic basis (e.g., every X hours, daily, etc.).

Figure 7:
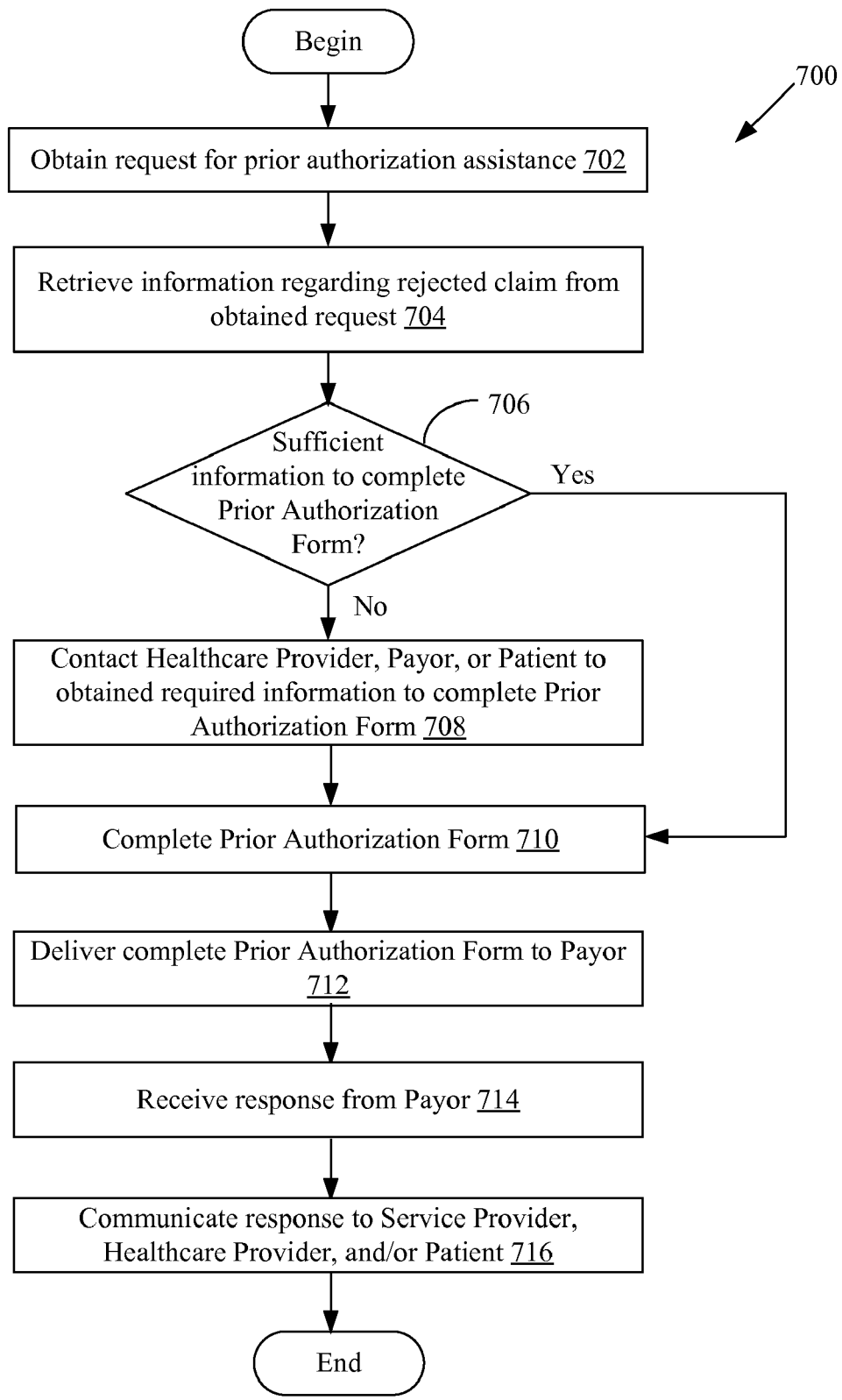
FIG. 7 illustrates a flow diagram of an example process that may be initiated to provide prior authorization assistance, according to an example embodiment of the invention.

FIG. 7 illustrates an example flow diagram 700 of a process that may be initiated to provide prior authorization assistance, according to an example embodiment of the invention. The process of FIG. 7 may be performed, either in whole or in part, by the prior authorization assistance computer 108, or a prior authorization assistance entity associated with the prior authorization assistance computer 108.

Turning now to FIG. 7, at block 700, the prior authorization assistance computer 108 may have received the request 253 for prior authorization assistance. As such, the prior authorization assistance computer 108 may obtain the request 253 from queue or memory. Following block 702 is block 704. At block 704, the information regarding the rejected claim may be obtained or retrieved from the request 253. As described herein, the request 253 can include one or more combinations of the following information:

Payor ID: Identification (e.g., name, BIN or BIN/PCN combination) of the payor that rejected the prescription claim request.
Patient Information
    Name (e.g., Patient Last Name, Patient First Name, etc.)
    Patient Address (e.g., Street Address, Zip Code, etc.)
    Patient Date of Birth (DOB) (or age of patient)
    Patient Gender Code
    Patient Contact Information (e.g., Patient Telephone Number)
    Patient ID or other identifier
Insurance/Coverage Information
    Cardholder Name (e.g., Cardholder First Name, Cardholder Last Name)
    Cardholder ID and/or other identifier (e.g., person code)
Healthcare Provider Information
    Prescriber ID or other identifier (e.g., NPI code, DEA number)
    Prescriber Name (e.g., Last Name, First Name)
    Prescriber Contact Information (e.g., telephone number, fax number, email address)
    Pharmacy/Pharmacist Information
    Pharmacy/Pharmacist ID (e.g., National Provider Identifier (NPI) code)

Pharmacy/Pharmacist Contact Information (e.g., telephone number, fax number, email address)

Claim Information

Reject Code (e.g., 75=Prior Authorization Required)

Drug or product information (e.g., National Drug Code (NDC))

Prescription/Service Reference Number

Date Prescription Written

Quantity Dispensed

Number of Days Supply

Diagnosis/Condition

Pricing information for the drug or product (e.g., network price, Usual & Customary price)

Date of Service.

Following block 704 is block 706. Block 706 may determine whether the retrieved information is sufficient to complete the appropriate prior authorization form. It will be appreciated that the information needed to complete the prior authorization form may depend upon the actual form that is supplied or requested by a payor. In addition, a payor may have multiple prior authorization forms, depending upon the diagnosis, condition, or type of drug or product. Accordingly, at block 704, the prior authorization assistance computer 108 and/or prior authorization entity may attempt to determine whether it can locate or identify the appropriate prior authorization form that needs to be completed. If the prior authorization form can be located or identified, then the prior authorization assistance computer 108 and/or prior authorization entity will determine whether the retrieved information is sufficient to complete the prior authorization form. In some example embodiments, the retrieved information can also be utilized to obtain or derive information from additional sources (e.g., healthcare provider databases) for use in completing the prior authorization form.

If block 706 determines that the appropriate prior authorization form can be identified, and that there is sufficient information to complete the prior authorization form, then processing will proceed to block 710, where the appropriate information obtained or derived from the request 253 is used to fill in the required fields of the appropriate prior authorization form. On the other hand, if the block 706 determines that there is insufficient information to complete the prior authorization form, then processing may proceed to block 708.

At block 708, the prior authorization assistance computer 108 may determine what missing information is needed. The request 253 may have identified the payor, patient, or healthcare provider (e.g., prescriber/doctor, pharmacist, etc.), as well as the respective contact information. Alternatively, the contact information for the payor, patient, and/or healthcare provider may be obtained from a different source (e.g., an external database) than the request 253. Depending upon the type of information needed, the prior authorization assistance computer 108 or an individual associated with a prior authorization entity may contact the payor, patient, or a healthcare provider to obtain the needed information. For example, the payor and/or claims processor computer 106 may be contacted to obtain the appropriate prior authorization form. Likewise, the patient may be contacted for additional information regarding a particular condition or diagnosis, or prior treatments. Likewise, a healthcare provider such as a prescriber or pharmacist (or associated computer) may be contacted to determine a particular condition/diagnosis for the patient. It will be appreciated that the payor, patient, or healthcare provider (or associated computer) can be contacted in a variety of communication means without departing from example embodiments of the invention. For example, the prior authorization assistance computer 108 can direct the delivery of a request in the form of an email, Internet message, fax, text message, telephone call, voice message to the payor, patient, or healthcare provider, or a computer associated therewith. The request may indicate what information is needed to complete a prior authorization request form, as well as the methods for providing the needed information to the prior authorization assistance entity or prior authorization assistance computer. In this regard, the payor, patient, or healthcare provider may be directed to a website to provide the needed information. Alternatively, the payor, patient, or healthcare provider can provide the needed information via email, Internet message, fax, telephone call, and the like.

Once the needed information is obtained at block 708, then processing may proceed to block 710, where the appropriate information obtained or derived from the request 253 and/or from block 708 is used to fill in the required fields of the appropriate prior authorization form. The completion of the prior authorization form may be performed by prior authorization assistance computer 108, where the completed prior authorization form may be in a text format, a PDF format, an HTML format, EDI format, or another electronic format. Alternatively, the prior authorization form can also be completed in paper form as well by an individual associated with the prior authorization assistance entity without departing from example embodiments of the invention.

Following block 710 is block 712, where the prior authorization assistance computer 108 or prior authorization assistance entity can deliver the completed prior authorization form to the appropriate payor or claims processor computer 106. It will be appreciated that the completed prior authorization form can be delivered electronically form the prior authorization assistance computer 108 to the claims processor computer 108 or another computer associated with the payor. In an example embodiment of the invention, the completed prior authorization form can be delivered as soon as it has been completed, or it may be batched with other completed prior authorization forms and delivered on a periodic basis to the claims processor computer 108 or another computer associated with the payor. The delivery of the completed prior authorization form can be via email, FTP or other Internet delivery, fax, EDI transmissions, or via other electronic communications means. Alternatively, the completed prior authorization form may be delivered from the prior authorization assistance entity to a payor through non-electronic communications means (e.g., paper delivery) without departing from example embodiments of the invention.

Following block 712 is block 714. At block 714, the claims processor computer 106 or payor may have received the completed prior authorization form, and provided a response to the prior authorization assistance computer 108. The response may take one of a variety of forms, such as but not including, (i) an indication that the completed prior authorization form has been received, and processing is in progress, (ii) an indication that the requested prior authorization has been approved, or (iii) an indication that the requested prior authorization has been denied. The response may be communicated from the claims processor computer 106 or other payor computer to the prior authorization assistance computer 108 through electronic communications means. At block 716, the prior authorization assistance computer 108 can communicate the received response to the service provider computer 104/prior authorization logic module 109, which in turn can communicate the response to the pharmacy computer 103, the patient, or another healthcare provider. Alternatively, the prior authorization assistance computer 108 can then communicate the received response directly to the pharmacy computer 103, the patient, or another healthcare provider. The communications may be via email, fax, text message, voice message, EDI transmissions, or other electronic communications without departing from example embodiments of the invention.

Once the prior authorization requested by the completed prior authorization form has been completed, then a pharmacy computer 102 can submit another prescription claim request 202 to the service provider computer 104, which in turn communicates the request to the claims processor computer as a request 203. Since the prior authorization for a particular drug or product for the patient has been approved, the claims processor computer 106 will provide a response 207 indicating approval of coverage. The response 207 will include the payor-covered amount as well as any patient-responsible amount. The service provider computer 104 may receive the response 207, and likewise communicate the response 207 to the pharmacy computer 103 as a response 103. The pharmacy can deliver the requested drug or product to the patient/customer at the pharmacy upon payment of any patient-responsible amount.

Figure 8:
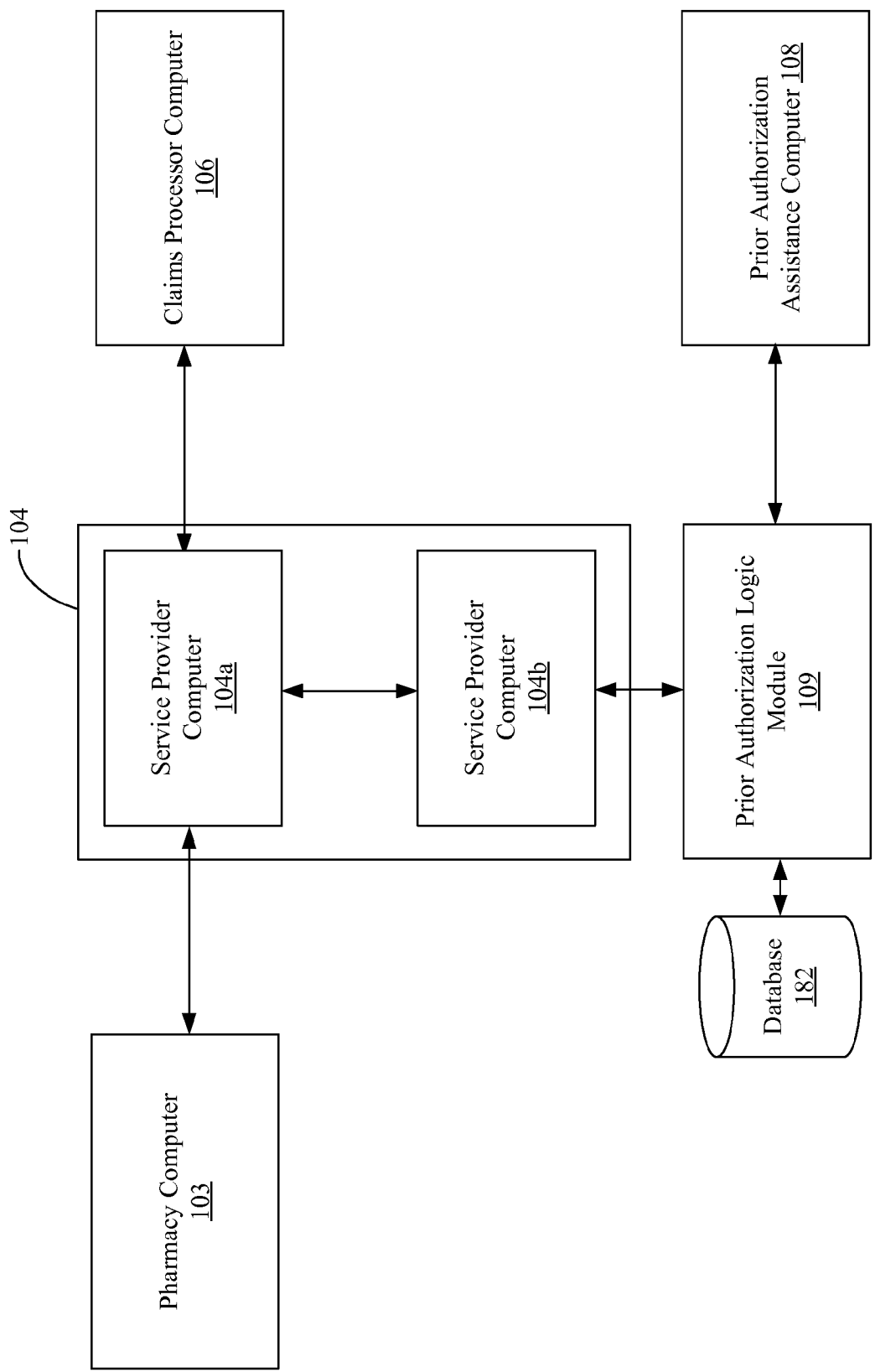
FIG. 8 illustrates a variation of the example block diagram of FIG. 2, according to an example embodiment of the invention

FIG. 8 illustrates a variation of the block diagrams of FIG. 2, according to an example embodiment of the invention. As shown by FIG. 8, the service provider computer 104 may be comprised of two or more distinct service provider computers 104a and 104b that are in communication with each other. Service provider computer 104a may be operative with the pharmacy computer 103 and claims processor(s) 106 while service provider computer 104b may be operative with other pharmacy computers and/or claims processors. However, service provider computer 104b may have a data processing arrangement with service provider computer 104a. Under the data processing agreement, the service provider computer 104a may be permitted to utilize or offer services of the service provider computer 104b, including the business rules described above and the prior authorization assistance logic module 109. Accordingly, the services of the service provider computer 104b, including the prior authorization assistance logic module 109 and the associated interactions with the prior authorization assistance computer 108, may be available to the pharmacy computer 103 via the service providers 104a and 104b.

The invention is described above with reference to block and flow diagrams of systems, methods, apparatuses, and/or computer program products according to example embodiments of the invention. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a general purpose computer, a special-purpose computer, a processor, or other programmable data processing apparatus to produce a particular machine, such that the instructions that execute on the computer, processor, or other programmable data processing apparatus create the means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer readable program code or program instructions embodied therein, said computer readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

It will be appreciated that each of the memories and data storage devices described herein can store data and information for subsequent retrieval. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices.

It will also be appreciated that each of the I/O interfaces described herein may facilitate communication between a processor and various I/O devices, such as a keyboard, mouse, printer, microphone, speaker, monitor, bar code readers/scanners, RFID readers, and the like. Likewise, each of the network interfaces described herein may take any of a number of forms, such as a network interface card, a modem, a wireless network card, and the like.

It will further be appreciated that while certain computers (e.g., computers 103, 104, 106) have been illustrated herein as a single computer or processor, the illustrated computers may actually be comprised of a group of computers or processors, according to an example embodiment of the invention.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method, comprising:
receiving a first request for prior authorization assistance from a pharmacy computer associated with a pharmacy, wherein the request for prior authorization assistance includes claim identification information for a prior healthcare claim transaction;

identifying a stored transaction history record for the prior healthcare claim transaction, wherein the stored transaction record is identified based at least in part on the claim identification information from the request for prior authorization assistance, wherein the stored transaction history record indicates a denial of coverage by a payor of a drug or product for a patient;

preparing a second request for prior authorization assistance, the second request based at least in part on information from the stored transaction history record, wherein the second request identifies at least patient information, identification of the drug or product for the patient, and identification of the payor;

delivering, to a prior authorization assistance computer, the second request for prior authorization assistance, wherein the information included in the second request enables the prior authorization assistance computer to initiate a process for completing a prior authorization form and for delivering the completed prior authorization form to the payor; and delivering, to the pharmacy computer, a response indicating acceptance of the first request for prior authorization assistance, wherein the response is stylized as a paid response or a rejection response based upon preferences of the pharmacy;

wherein the prior steps are performed by one or more computers associated with a service provider.

2. The method of claim 1, wherein one or both of the first request for prior authorization assistance and the second request for prior authorization assistance is in a form of a billing claim request conventionally utilized for requesting financial reimbursement.

3. The method of claim 2, wherein one or both of the first request and the second request utilize a particular BIN Number or combination of the particular BIN Number and a Processor Control Number (PCN) to indicate a request for prior authorization assistance.

4. The method of claim 1, wherein prior to receiving the first request for prior authorization assistance, the method further includes:

receiving a healthcare claim request from the healthcare provider computer, wherein the healthcare transaction request identifies the drug or product for the patient;

delivering the healthcare claim request to a claims processor computer associated with the payor for processing or adjudication;

receiving a rejection response for the healthcare transaction request from the claims processor computer, wherein the healthcare transaction request and the rejection response are part of a healthcare transaction, wherein the rejection response includes a reject code that indicates the denial of coverage for the drug or product;

determining, based at least in part upon the reject code and the identified drug or product, that the healthcare transaction is qualified for prior authorization assistance; and storing, based upon the determination, the transaction history record, wherein the transaction history record includes information from one or both of the healthcare claim request and the rejection response, wherein the prior steps are performed by one or more computers associated with a service provider.

5. The method of claim 4, further comprising:

delivering a second response to the pharmacy computer, the second response indicating the denial of coverage for the drug or product and an availability of prior authorization assistance, wherein the prior step is performed by one or more computers associated with a service provider.

6. The method of claim 4, wherein the prior authorization assistance computer is either (i) part of the one or more computers of the service provider, or (ii) another computer of the service provider.

7. The method of claim 4, wherein the prior authorization form is further completed using information from the identified stored transaction history record.

8. The method of claim 4, wherein both the claim identification information and the stored transaction history record includes at least (i) an identifier of the payor, (ii) an identifier of the drug or product, (iii) a date of service, (iv) a prescription/service reference number, and (v) an identifier of the pharmacy.

9. The method of claim 1, further comprising:

receiving a second response from the prior authorization computer, the second response indicating one of (i) receipt of the completed prior authorization form, (ii) delivery of the completed prior authorization form to the payor, or (iii) a result of the payor processing the completed prior authorization form; and delivering information from the second response to the pharmacy computer, wherein the prior steps are performed by one or more computers associated with a service provider.

10. The method of claim 1, wherein the response is stylized as the paid response, wherein the patient-responsible amount of the paid response is set to a full price of the drug or product.

11. A system, comprising:

at least one memory for storing computer-executable instructions;

at least one processor configured to access the at least one memory and execute the computer-executable instructions to:

receive a first request for prior authorization assistance from a pharmacy computer associated with a pharmacy, wherein the request for prior authorization assistance includes claim identification information for a prior healthcare claim transaction;

identify a stored transaction history record for the prior healthcare claim transaction, wherein the stored transaction record is identified based at least in part on the claim identification information from the request for prior authorization assistance, wherein the stored transaction history record indicates a denial of coverage by a payor of a drug or product for a patient;

prepare a second request for prior authorization assistance, the second request based at least in part on information from the stored transaction history record, wherein the second request identifies at least patient information, identification of the drug or product for the patient, and identification of the payor;

deliver, to a prior authorization assistance computer, the second request for prior authorization assistance, wherein the information included in the second request enables the prior authorization assistance computer to initiate a process for completing a prior authorization form and for delivering the completed prior authorization form to the payor; and deliver, to the pharmacy computer, a response indicating acceptance of the first request for prior authorization assistance, wherein the response is stylized as a paid response or a rejection response based upon preferences of the pharmacy.

12. The system of claim 11, wherein one or both of the first request for prior authorization assistance and the second request for prior authorization assistance is in a form of a billing claim request conventionally utilized for requesting financial reimbursement.

13. The system of claim 12, wherein one or both of the first request and the second request utilize a particular BIN Number or combination of the particular BIN Number and a Processor Control Number (PCN) to indicate a request for prior authorization assistance.

14. The system of claim 11, wherein prior to receiving the first request for prior authorization assistance, the at least one processor is further configured to execute the computer-executable instructions to:
receive a healthcare claim request from the healthcare provider computer, wherein the healthcare transaction request identifies the drug or product for the patient;
deliver the healthcare claim request to a claims processor computer associated with the payor for processing or adjudication;
receive a rejection response for the healthcare transaction request from the claims processor computer, wherein the healthcare transaction request and the rejection response are part of a healthcare transaction, wherein the rejection response includes a reject code that indicates the denial of coverage for the drug or product;
determine, based at least in part upon the reject code and the identified drug or product, that the healthcare transaction is qualified for prior authorization assistance; and
store, based upon the determination, the transaction history record, wherein the transaction history record includes information from one or both of the healthcare claim request and the rejection response.

15. The system of claim 14, wherein the at least one processor is further configured to execute the computer-executable instructions to:
deliver a second response to the pharmacy computer, the second response indicating the denial of coverage for the drug or product and an availability of prior authorization assistance.

16. The system of claim 14, wherein the at least one processor is part of one or more computers of a service provider.

17. The system of claim 14, wherein the prior authorization form is further completed using information from the identified stored transaction history record.

18. The system of claim 14, wherein both the claim identification information and the stored transaction history record includes at least (i) an identifier of the payor, (ii) an identifier of the drug or product, (iii) a date of service, (iv) a prescription/service reference number, and (v) an identifier of the pharmacy.

19. The system of claim 11, wherein the at least one processor is further configured to execute the computer-executable instructions to:
receive a second response from the prior authorization computer, the second response indicating one of (i) receipt of the completed prior authorization form, (ii) delivery of the completed prior authorization form to the payor, or (iii) a result of the payor processing the completed prior authorization form; and
deliver information from the second response to the pharmacy computer.

20. The system of claim 11, wherein the response is stylized as the paid response, wherein the patient-responsible amount of the paid response is set to a full price of the drug or product.

\* \* \* \* \*